(12) United States Patent
Park et al.

(10) Patent No.: US 8,765,402 B2
(45) Date of Patent: *Jul. 1, 2014

(54) COPOLYMER CONTAINING 3-HYDROXYALKANOATE UNIT AND LACTATE UNIT, AND ITS MANUFACTURING METHOD

(75) Inventors: Si-Jae Park, Daejeon (KR); Taek-Ho Yang, Daejeon (KR); Hye-Ok Kang, Daejeon (KR); Sang-Hyun Lee, Daejeon (KR); Eun-Jeong Lee, Daejeon (KR); Tae-Wan Kim, Daejeon (KR); Sang-Yup Lee, Daejeon (KR)

(73) Assignee: LG Chem, Ltd., Seoul (KR)

(*) Notice: Subject to any disclaimer, the term of this patent is extended or adjusted under 35 U.S.C. 154(b) by 1344 days.

This patent is subject to a terminal disclaimer.

(21) Appl. No.: 12/312,636

(22) PCT Filed: Nov. 21, 2007

(86) PCT No.: PCT/KR2007/005853
§ 371 (c)(1),
(2), (4) Date: Nov. 12, 2010

(87) PCT Pub. No.: WO2008/062996
PCT Pub. Date: May 29, 2008

(65) Prior Publication Data
US 2011/0046339 A1 Feb. 24, 2011

(30) Foreign Application Priority Data

Nov. 21, 2006 (KR) .................. 10-2006-0115162
Nov. 21, 2006 (KR) .................. 10-2006-0115163
Nov. 21, 2006 (KR) .................. 10-2006-0115164
Nov. 23, 2006 (KR) .................. 10-2006-0116232
Nov. 23, 2006 (KR) .................. 10-2006-0116233

(51) Int. Cl.
*C12P 1/04* (2006.01)

(52) U.S. Cl.
USPC ........................................... 435/41

(58) Field of Classification Search
None
See application file for complete search history.

(56) References Cited

U.S. PATENT DOCUMENTS

| 5,516,883 A | 5/1996 | Hori et al. | |
|---|---|---|---|
| 2010/0222545 A1* | 9/2010 | Park et al. | 528/361 |

FOREIGN PATENT DOCUMENTS

| JP | 06-016790 | 1/1994 |
|---|---|---|
| JP | 06-329768 | 11/1994 |
| JP | 09-304253 | 11/1994 |
| JP | 2002-008428 | 1/2002 |
| WO | WO 2006/126796 | 11/2006 |

OTHER PUBLICATIONS

Noda et al, 2004, Macromol. Biosci., 4:269-275.*
Taguchi et al, 2008, PNAS, 105:17323-17327.*
Selmer et al, 2002, Eur. J. Biochem., 269: 372-380.*
Yang et al, 2010, Biotech and Bioeng., 105: 150-160.*
Valentin et al, 1994, Appl. Microbiol. Biotechnol., 40:699-709.*
Snell et al, 2002, Metabolic Engineering, 4:29-40.*
Noda et al, 2004, Macromolecular Bioscience, 4:269-275.*
Song et al, 2004, "Cloning of new *Pseudomonas* sp. MBEL 6-19 polyhydroxyalkanoate synthase genes and their use in the development of recombinant proteins", Abstract.*
"Physical properties and enzymatic degradability of copolymers of (R)-3-hydroxybutyric acid and (S,S)-Lactide", Hideki Abe, et al., Polymer, Issue 1, vol. 39, pp. 59-67, Dec. 31, 1997.

* cited by examiner

*Primary Examiner* — Ashwin Mehta
*Assistant Examiner* — Jason Deveau Rosen
(74) *Attorney, Agent, or Firm* — McKenna Long & Aldridge, LLP

(57) ABSTRACT

The present invention relates to a copolymer comprising 3-hydroxyalkanoate monomer unit and lactate monomer unit, or their preparing method. More specifically, the present invention relates to a method for preparing a copolymer comprising lactate monomer and 3-hydroxyalkanoate monomer, wherein the method comprises culturing a cell or plant comprising the gene of enzyme converting lactate and 3-hydroxyalkanoate into lactyl-CoA and 3-hydroxyalkanoyl-CoA, respectively, and polyhydroxyalkanoate synthase gene together, and the copolymer made by the method. The copolymer of the present invention is a biodegradable polymer being able to be usefully used instead of conventional synthetic plastic, and the copolymer can be used also for medical use.

8 Claims, 5 Drawing Sheets

SEQUENCE LISTING

<160> NUMBER OF SEQ ID NOS: 38

<210> SEQ ID NO 1
<211> LENGTH: 39
<212> TYPE: DNA
<213> ORGANISM: Artificial Sequence
<220> FEATURE:
<223> OTHER INFORMATION: primer

<400> SEQUENCE: 1

```
ggaattcatg agaaaggttc ccattattac cgcagatga                           39

<210> SEQ ID NO 2
<211> LENGTH: 46
<212> TYPE: DNA
<213> ORGANISM: Artificial Sequence
<220> FEATURE:
<223> OTHER INFORMATION: primer

<400> SEQUENCE: 2
gctctagatt aggacttcat ttccttcaga cccattaagc cttctg                  46

<210> SEQ ID NO 3
<211> LENGTH: 32
<212> TYPE: DNA
<213> ORGANISM: Artificial Sequence
<220> FEATURE:
<223> OTHER INFORMATION: primer

<400> SEQUENCE: 3
aggcctgcag gcggataaca atttcacaca gg                                 32

<210> SEQ ID NO 4
<211> LENGTH: 31
<212> TYPE: DNA
<213> ORGANISM: Artificial Sequence
<220> FEATURE:
<223> OTHER INFORMATION: primer

<400> SEQUENCE: 4
gcccatatgt ctagattagg acttcatttc c                                  31

<210> SEQ ID NO 5
<211> LENGTH: 35
<212> TYPE: DNA
<213> ORGANISM: Artificial Sequence
<220> FEATURE:
<223> OTHER INFORMATION: primer

<400> SEQUENCE: 5
gagagacaat caaatcatga gtaacaagag taacg                              35

<210> SEQ ID NO 6
<211> LENGTH: 33
<212> TYPE: DNA
<213> ORGANISM: Artificial Sequence
<220> FEATURE:
<223> OTHER INFORMATION: primer

<400> SEQUENCE: 6
cactcatgca agcgtcaccg ttcgtgcacg tac                                33

<210> SEQ ID NO 7
<211> LENGTH: 1677
<212> TYPE: DNA
<213> ORGANISM: Pseudomonas sp. 6-19 (KCTC11027BP)

<400> SEQUENCE: 7
atgagtaaca agagtaacga tgagttgaag tatcaagcct ctgaaaacac cttggggctt    60
aatcctgtcg ttgggctgcg tggaaaggat ctactggctt ctgctcgaat ggtgcttagg   120
caggccatca gcaaccggt gcacagcgtc aaacatgtcg cgcactttgg tcttgaactc   180
aagaacgtac tgctgggtaa atccgggctg caaccgacca gcgatgaccg tcgcttcgcc   240
gatccggcct ggagccagaa cccgctctat aaacgttatt tgcaaaccta cctggcgtgg   300
```

```
cgcaaggaac tccacgactg gatcgatgaa agtaacctcg ccccaagga tgtggcgcgt    360 gggcacttcg tgatcaacct catgaccgaa gcgatggcgc cgaccaacac gcggccaac    420 ccggcggcag tcaaacgctt ttttgaaacc ggtggcaaaa gcctgctcga cggcctctcg    480
cacctggcca aggatctggt acacaacggc ggcatgccga gccaggtcaa catgggtgca    540
ttcgaggtcg gcaagagcct gggcgtgacc gaaggcgcgg tggtgtttcg caacgatgtg    600
ctggaactga tccagtacaa gccgaccacc gagcaggtat acgaacgccc gctgctggtg    660
gtgccgccgc agatcaacaa gttctacgtt ttcgacctga gcccggacaa gagcctggcg    720
cggttctgcc tgcgcaacaa cgtgcaaacg ttcatcgtca gctggcgaaa tcccaccaag    780
gaacagcgag agtggggcct gtcgacctac atcgaagccc tcaaggaagc ggttgacgtc    840
gttaccgcga tcaccggcag caaagacgtg aacatgctcg gggcctgctc cggcggcatc    900
acttgcactg cgctgctggg ccattacgcg gcgattggcg aaaacaaggt caacgccctg    960
accttgctgg tgagcgtgct tgataccacc ctcgacagcg acgtcgccct gttcgtcaat   1020
gaacagaccc ttgaagccgc caagcgccac tcgtaccagg ccggcgtact ggaaggccgc   1080
gacatggcga aggtcttcgc ctggatgcgc cccaacgatc tgatctggaa ctactgggtc   1140
aacaattacc tgctaggcaa cgaaccgccg gtgttcgaca tcctgttctg gaacaacgac   1200
accacacggt tgcccgcggc gttccacggc gacctgatcg aactgttcaa aaataaccca   1260
ctgattcgcc cgaatgcact ggaagtgtgc ggcaccccca tcgacctcaa gcaggtgacg   1320
gccgacatct tttccctggc cggcaccaac gaccacatca cccgtggaa gtcctgctac   1380 aagtcggcgc aactgtttgg cggcaacgtt gaattcgtgc tgtcgagcag cgggcatatc   1440
cagagcatcc tgaaccccgc gggcaatccg aaatcgcgct acatgaccag caccgaagtg   1500
gcggaaaatg ccgatgaatg caagcgaat gccaccaagc atacagattc ctggtggctg   1560
cactggcagg cctggcaggc caacgctcg ggcgagctga aaaagtcccc gacaaaactg   1620
ggcagcaagg cgtatccggc aggtgaagcg gcgccaggca cgtacgtgca cgaacgg     1677
```

<210> SEQ ID NO 8
<211> LENGTH: 559
<212> TYPE: PRT
<213> ORGANISM: Pseudomonas sp. 6-19 (KCTC11027BP)

<400> SEQUENCE: 8

```
Met Ser Asn Lys Ser Asn Asp Glu Leu Lys Tyr Gln Ala Ser Glu Asn
  1               5                  10                  15

Thr Leu Gly Leu Asn Pro Val Val Gly Leu Arg Gly Lys Asp Leu Leu
             20                  25                  30

Ala Ser Ala Arg Met Val Leu Arg Gln Ala Ile Lys Gln Pro Val His
         35                  40                  45

Ser Val Lys His Val Ala His Phe Gly Leu Glu Leu Lys Asn Val Leu
     50                  55                  60

Leu Gly Lys Ser Gly Leu Gln Pro Thr Ser Asp Asp Arg Arg Phe Ala
 65                  70                  75                  80

Asp Pro Ala Trp Ser Gln Asn Pro Leu Tyr Lys Arg Tyr Leu Gln Thr
                 85                  90                  95

Tyr Leu Ala Trp Arg Lys Glu Leu His Asp Trp Ile Asp Glu Ser Asn
            100                 105                 110

Leu Ala Pro Lys Asp Val Ala Arg Gly His Phe Val Ile Asn Leu Met
        115                 120                 125
```

```
Thr Glu Ala Met Ala Pro Thr Asn Thr Ala Ala Asn Pro Ala Ala Val
            130                 135                 140

Lys Arg Phe Phe Glu Thr Gly Gly Lys Ser Leu Leu Asp Gly Leu Ser
145                 150                 155                 160

His Leu Ala Lys Asp Leu Val His Asn Gly Gly Met Pro Ser Gln Val
                165                 170                 175

Asn Met Gly Ala Phe Glu Val Gly Lys Ser Leu Gly Val Thr Glu Gly
            180                 185                 190

Ala Val Val Phe Arg Asn Asp Val Leu Glu Leu Ile Gln Tyr Lys Pro
            195                 200                 205

Thr Thr Glu Gln Val Tyr Glu Arg Pro Leu Leu Val Val Pro Pro Gln
    210                 215                 220

Ile Asn Lys Phe Tyr Val Phe Asp Leu Ser Pro Asp Lys Ser Leu Ala
225                 230                 235                 240

Arg Phe Cys Leu Arg Asn Asn Val Gln Thr Phe Ile Val Ser Trp Arg
                245                 250                 255

Asn Pro Thr Lys Glu Gln Arg Glu Trp Gly Leu Ser Thr Tyr Ile Glu
            260                 265                 270

Ala Leu Lys Glu Ala Val Asp Val Val Thr Ala Ile Thr Gly Ser Lys
            275                 280                 285

Asp Val Asn Met Leu Gly Ala Cys Ser Gly Gly Ile Thr Cys Thr Ala
    290                 295                 300

Leu Leu Gly His Tyr Ala Ala Ile Gly Glu Asn Lys Val Asn Ala Leu
305                 310                 315                 320

Thr Leu Leu Val Ser Val Leu Asp Thr Thr Leu Asp Ser Asp Val Ala
                325                 330                 335

Leu Phe Val Asn Glu Gln Thr Leu Glu Ala Ala Lys Arg His Ser Tyr
            340                 345                 350

Gln Ala Gly Val Leu Glu Gly Arg Asp Met Ala Lys Val Phe Ala Trp
            355                 360                 365

Met Arg Pro Asn Asp Leu Ile Trp Asn Tyr Trp Val Asn Asn Tyr Leu
    370                 375                 380

Leu Gly Asn Glu Pro Pro Val Phe Asp Ile Leu Phe Trp Asn Asn Asp
385                 390                 395                 400

Thr Thr Arg Leu Pro Ala Ala Phe His Gly Asp Leu Ile Glu Leu Phe
                405                 410                 415

Lys Asn Asn Pro Leu Ile Arg Pro Asn Ala Leu Glu Val Cys Gly Thr
            420                 425                 430

Pro Ile Asp Leu Lys Gln Val Thr Ala Asp Ile Phe Ser Leu Ala Gly
            435                 440                 445

Thr Asn Asp His Ile Thr Pro Trp Lys Ser Cys Tyr Lys Ser Ala Gln
    450                 455                 460

Leu Phe Gly Gly Asn Val Glu Phe Val Leu Ser Ser Gly His Ile
465                 470                 475                 480

Gln Ser Ile Leu Asn Pro Pro Gly Asn Pro Lys Ser Arg Tyr Met Thr
            485                 490                 495

Ser Thr Glu Val Ala Glu Asn Ala Asp Glu Trp Gln Ala Asn Ala Thr
            500                 505                 510

Lys His Thr Asp Ser Trp Trp Leu His Trp Gln Ala Trp Gln Ala Gln
    515                 520                 525

Arg Ser Gly Glu Leu Lys Lys Ser Pro Thr Lys Leu Gly Ser Lys Ala
530                 535                 540

Tyr Pro Ala Gly Glu Ala Ala Pro Gly Thr Tyr Val His Glu Arg
```

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
atgcccggag ccggttcgaa                                               20

<210> SEQ ID NO 10
<211> LENGTH: 35
<212> TYPE: DNA
<213> ORGANISM: Artificial Sequence
<220> FEATURE:
<223> OTHER INFORMATION: primer

<400> SEQUENCE: 10
cgttactctt gttactcatg atttgattgt ctctc                              35

<210> SEQ ID NO 11
<211> LENGTH: 35
<212> TYPE: DNA
<213> ORGANISM: Artificial Sequence
<220> FEATURE:
<223> OTHER INFORMATION: primer

<400> SEQUENCE: 11
gagagacaat caaatcatga gtaacaagag taacg                              35

<210> SEQ ID NO 12
<211> LENGTH: 33
<212> TYPE: DNA
<213> ORGANISM: Artificial Sequence
<220> FEATURE:
<223> OTHER INFORMATION: primer

<400> SEQUENCE: 12
cactcatgca agcgtcaccg ttcgtgcacg tac                                33

<210> SEQ ID NO 13
<211> LENGTH: 33
<212> TYPE: DNA
<213> ORGANISM: Artificial Sequence
<220> FEATURE:
<223> OTHER INFORMATION: primer

<400> SEQUENCE: 13
gtacgtgcac gaacggtgac gcttgcatga gtg                                33

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
aacgggaggg aacctgcagg                                               20

<210> SEQ ID NO 15
<211> LENGTH: 33
<212> TYPE: DNA
<213> ORGANISM: Artificial Sequence

```
<220> FEATURE:
<223> OTHER INFORMATION: primer

<400> SEQUENCE: 15
atcaacctca tgaccgatgc gatggcgccg acc                                33

<210> SEQ ID NO 16
<211> LENGTH: 33
<212> TYPE: DNA
<213> ORGANISM: Artificial Sequence
<220> FEATURE:
<223> OTHER INFORMATION: primer

<400> SEQUENCE: 16
ggtcggcgcc atcgcatcgg tcatgaggtt gat                                33

<210> SEQ ID NO 17
<211> LENGTH: 33
<212> TYPE: DNA
<213> ORGANISM: Artificial Sequence
<220> FEATURE:
<223> OTHER INFORMATION: primer

<400> SEQUENCE: 17
ctgaccttgc tggtgaccgt gcttgatacc acc                                33

<210> SEQ ID NO 18
<211> LENGTH: 33
<212> TYPE: DNA
<213> ORGANISM: Artificial Sequence
<220> FEATURE:
<223> OTHER INFORMATION: primer

<400> SEQUENCE: 18
ggtggtatca agcacggtca ccagcaaggt cag                                33

<210> SEQ ID NO 19
<211> LENGTH: 36
<212> TYPE: DNA
<213> ORGANISM: Artificial Sequence
<220> FEATURE:
<223> OTHER INFORMATION: primer

<400> SEQUENCE: 19
cgagcagcgg gcatatcatg agcatcctga acccgc                             36

<210> SEQ ID NO 20
<211> LENGTH: 36
<212> TYPE: DNA
<213> ORGANISM: Artificial Sequence
<220> FEATURE:
<223> OTHER INFORMATION: primer

<400> SEQUENCE: 20
gcgggttcag gatgctcatg atatgcccgc tgctcg                             36

<210> SEQ ID NO 21
<211> LENGTH: 34
<212> TYPE: DNA
<213> ORGANISM: Artificial Sequence
<220> FEATURE:
<223> OTHER INFORMATION: Primer

<400> SEQUENCE: 21
ggaaatccat atgacgatgt tctcgctcat ggcg                               34
```

```
<210> SEQ ID NO 22
<211> LENGTH: 37
<212> TYPE: DNA
<213> ORGANISM: Artificial Sequence
<220> FEATURE:
<223> OTHER INFORMATION: Primer

<400> SEQUENCE: 22
ggaaatccat atgatccagg gccactatct ccaactg                              37

<210> SEQ ID NO 23
<211> LENGTH: 30
<212> TYPE: DNA
<213> ORGANISM: Artificial Sequence
<220> FEATURE:
<223> OTHER INFORMATION: Primer

<400> SEQUENCE: 23
gaattcgtgc tgtcgagccg cgggcatatc                                       30

<210> SEQ ID NO 24
<211> LENGTH: 30
<212> TYPE: DNA
<213> ORGANISM: Artificial Sequence
<220> FEATURE:
<223> OTHER INFORMATION: Primer

<400> SEQUENCE: 24
gatatgcccg cggctcgaca gcacgaattc                                       30

<210> SEQ ID NO 25
<211> LENGTH: 30
<212> TYPE: DNA
<213> ORGANISM: Artificial Sequence
<220> FEATURE:
<223> OTHER INFORMATION: Primer

<400> SEQUENCE: 25
gaattcgtgc tgtcgagcca tgggcatatc                                       30

<210> SEQ ID NO 26
<211> LENGTH: 30
<212> TYPE: DNA
<213> ORGANISM: Artificial Sequence
<220> FEATURE:
<223> OTHER INFORMATION: Primer

<400> SEQUENCE: 26
gatatgccca tggctcgaca gcacgaattc                                       30

<210> SEQ ID NO 27
<211> LENGTH: 30
<212> TYPE: DNA
<213> ORGANISM: Artificial Sequence
<220> FEATURE:
<223> OTHER INFORMATION: Primer

<400> SEQUENCE: 27
gaattcgtgc tgtcgagctt tgggcatatc                                       30

<210> SEQ ID NO 28
<211> LENGTH: 30
<212> TYPE: DNA
<213> ORGANISM: Artificial Sequence
<220> FEATURE:
<223> OTHER INFORMATION: Primer
```

<210> SEQ ID NO 28 gatatgccca aagctcgaca gcacgaattc     30

<210> SEQ ID NO 29
<211> LENGTH: 30
<212> TYPE: DNA
<213> ORGANISM: Artificial Sequence
<220> FEATURE:
<223> OTHER INFORMATION: Primer

<400> SEQUENCE: 29
gaattcgtgc tgtcgagcta tgggcatatc     30

<210> SEQ ID NO 30
<211> LENGTH: 30
<212> TYPE: DNA
<213> ORGANISM: Artificial Sequence
<220> FEATURE:
<223> OTHER INFORMATION: Primer

<400> SEQUENCE: 30
gatatgccca tagctcgaca gcacgaattc     30

<210> SEQ ID NO 31
<211> LENGTH: 30
<212> TYPE: DNA
<213> ORGANISM: Artificial Sequence
<220> FEATURE:
<223> OTHER INFORMATION: Primer

<400> SEQUENCE: 31
gaattcgtgc tgtcgagcgg cgggcatatc     30

<210> SEQ ID NO 32
<211> LENGTH: 30
<212> TYPE: DNA
<213> ORGANISM: Artificial Sequence
<220> FEATURE:
<223> OTHER INFORMATION: Primer

<400> SEQUENCE: 32
gatatgcccg ccgctcgaca gcacgaattc     30

<210> SEQ ID NO 33
<211> LENGTH: 28
<212> TYPE: DNA
<213> ORGANISM: Artificial Sequence
<220> FEATURE:
<223> OTHER INFORMATION: Primer

<400> SEQUENCE: 33
gggcatatca aaagcatcct gaacccgc     28

<210> SEQ ID NO 34
<211> LENGTH: 28
<212> TYPE: DNA
<213> ORGANISM: Artificial Sequence
<220> FEATURE:
<223> OTHER INFORMATION: Primer

<400> SEQUENCE: 34
gcgggttcag gatgcttttg atatgccc     28

<210> SEQ ID NO 35

```
<211> LENGTH: 28
<212> TYPE: DNA
<213> ORGANISM: Artificial Sequence
<220> FEATURE:
<223> OTHER INFORMATION: Primer

<400> SEQUENCE: 35
gggcatatca tgagcatcct gaacccgc                                          28

<210> SEQ ID NO 36
<211> LENGTH: 28
<212> TYPE: DNA
<213> ORGANISM: Artificial Sequence
<220> FEATURE:
<223> OTHER INFORMATION: Primer

<400> SEQUENCE: 36
gcgggttcag gatgctcatg atatgccc                                          28

<210> SEQ ID NO 37
<211> LENGTH: 28
<212> TYPE: DNA
<213> ORGANISM: Artificial Sequence
<220> FEATURE:
<223> OTHER INFORMATION: Primer

<400> SEQUENCE: 37
gggcatatcc gcagcatcct gaacccgc                                          28

<210> SEQ ID NO 38
<211> LENGTH: 28
<212> TYPE: DNA
<213> ORGANISM: Artificial Sequence
<220> FEATURE:
<223> OTHER INFORMATION: Primer

<400> SEQUENCE: 38
gcgggttcag gatgctgcgg atatgccc                                          28
```

COPOLYMER CONTAINING 3-HYDROXYALKANOATE UNIT AND LACTATE UNIT, AND ITS MANUFACTURING METHOD

This application claims priority to International Patent Application No. PCT/KR2007/005853 filed on Nov. 21, 2007 along with Korean Patent Application Nos. 10-2006-0115162, 10-2006-0115163 and 10-2006-0115164 filed on Nov. 21, 2006; and 10-2006-0116232 and 10-2006-0116233 filed on Nov. 23, 2006, all of which contents are hereby incorporated by reference in their entirety.

TECHNICAL FIELD

The present invention relates to copolymer comprising 3-hydroxyalkanoate monomer unit and lactate monomer unit, and a method for manufacturing such polymer.

BACKGROUND ART

Polylactate (PLA) is a typical biodegradable polymer originated from lactate, which has a variety of applications as a common or a medical polymer. At present, PLA is being prepared by polymerizing lactate which is produced by fermenting microorganisms, but only low molecular weight PLA (1000-5000 dalton) is produced by direct polymerization of lactate. To synthesize high molecular weight (>100,000 dalton) of PLA, a method polymerizing low molecular weight PLA obtained by direct polymerization of lactate with a chain coupling agent can be used. However, it has disadvantages like that the process for preparing PLA of high molecular weight is complicated due to the addition of a solvent or a chain coupling agent, and also it isn't easy to remove them. At present, in the process for preparing commercially available PLA of high molecular weight, a method, in which lactate is converted into lactide to synthesize PLA by cyclodehydration of the lactide ring, is being used.

Meanwhile, polyhydroxyalkanoate (PHA) is a polyester which microorganisms accumulate therein as a carbon and energy storage compound when other nutritive elements, for example, phosphorus, nitrogen, magnesium, oxygen, are deficient while the carbon source is in excess. PHA is recognized as an alternative material for synthesized plastics since it has similar properties to synthetic polymers originating from petroleum, and, at the same time, shows an excellent biodegradation property.

The existing PHA is divided into SCL-PHA (short-chain-length PHA) having short carbon chains and MCL-PHA (medium-chain-length PHA) having long carbon chains. A gene synthesizing PHA was cloned from *Ralstonia eutropha*, *Pseudomonas* sp. Microorganism, and PHA consisting of various monomers was synthesized by recombinant microorganisms (Qi et al., *FEMS Microbiol. Lett.*, 157:155, 1997; Qi et al., *FEMS Microbiol. Lett.*, 167:89, 1998; Langenbach et al., *FEMS Microbiol. Lett.*, 150:303, 1997; WO 01/55436; U.S. Pat. No. 6,143,952; WO 98/54329; and WO 99/61624).

To produce PHA in microorganisms, an enzyme which converts microorganisms' metabolites into a PHA monomer and PHA synthase which synthesizes a PHA polymer using the PHA monomers are required. PHA synthase synthesizes PHA using hydroxyacyl-CoA as a substrate and alpha-ketothiolase (PhaA), acetoacetyl-CoA reductase (PhaB), cloned from *Ralstonia eutropha* etc., 3-hydroxydecanoyl-ACP:CoA transferase (PhaG) cloned from *Pseudomonas* sp., (R)-specific enoyl-CoA hydratase (PhaJ) derived from *Aeromonas caviae* and *Pseudomonas aeruginosa* (Fukui et al., J. Bacteriol., 180:667, 1998; Tsage et al., FEMS Microbiol. Lett., 184:193, 2000), 3-ketoacyl-ACP reductase (FabG) derived from *E. coli*, *Pseudomonas aeruginosa*, etc. (Taguchi et al., FEMS Microbiol. Lett., 176:183, 1999; Ren et al., J. Bacteriol., 182:2978, 2000; Park et al., FEMS Microbiol. Lett., 214:217, 2002), phosphotransbutylase (Ptb) and butyrate kinase (Buk) derived from *Clostridium acetobutyricum* (Liu and Steinbuchel, Appl Environ Microbiol, 66:739, 2000), Cat2 derived from *Clostridium kluyveri* (Hein et al. FEMS Microbiol. Lett., 15:411, 1997), etc. are known as enzymes capable of generating hydroxyacyl-CoA which is a substrate of PHA.

Various kinds of PHAs have been synthesized with these enzymes using hydroxyalkanoates hydroxylated at various positions in the carbon chain (mainly the 3, 4, 5, and 6 positions).

However, it has been reported that it has little PHA synthase activity on hydroxyalkanoate which is hydroxylated at the 2-position (Zhang et al., Appl. Microbiol. Biotechnol., 56:131, 2001; Valentin and Steinbuchel, Appl. Microbiol. Biotechnol., 40:699, 1994). Thus far, there have been reports of PHA synthase activity on lactyl-CoA measured in vitro, but PHA synthase activity on lactyl-CoA is very weak (Zhang et al., Appl. Microbiol. Biotechnol., 56:131, 2001; Valentin and Steinbuchel, Appl. Microbiol. Biotechnol., 40:699, 1994). That is, there are no examples of natural production or production by recombinant cells of PHA and its copolymers because a hydroalkanoate, such as lactate hydroxylated at the 2-carbon position, is not a suitable substrate for PHA synthase.

DISCLOSURE

Technical Problem

Accordingly, the object of the present invention is to provide a copolymer comprising 3-hydroxyalkanoate monomer unit and lactate monomer unit.

Another object of the present invention is to provide a method for efficiently preparing a copolymer comprising 3-hydroxyalkanoate monomer unit and lactate monomer unit.

Technical Solution

To achieve the object, the present invention provides a copolymer comprising lactate monomer unit and 3-hydroxyalkanoate monomer unit, and preferably, the 3-hydroxyalkanoate is at least one selected from the group consisting of 3-hydroxybutyrate, 3-hydroxyvalerate, 3-hydroxypropionate and medium chain length (MCL) of 3-hydroxyalkanoate.

The term "copolymer," as used herein, is meant to include bipolymer consisting of two distinct monomers, terpolymer consisting of three distinct monomers or tetrapolymer consisting of four distinct monomers.

Further, the medium chain length (MCL) of 3-hydroxyalkanoate may be at least one selected from the group consisting of 3-hydroxyhexanoate (3HHx), 3-hydroxyheptanoate (3HHp), 3-hydroxyoctanoate (3HO), 3-hydroxynonanoate (3HN), 3-hydroxydecanoate (3HD), 3-hydroxyundecanoate (3HUD) and 3-hydroxydodecanoate (3HDD), but to which the present invention is not limited.

More preferably, the present invention provides MCL 3-hydroxyalkanoate-lactate copolymer (poly(MCL 3-hydroxyalkanoate-co-lactate)), 3-hydroxybutyrate-medium chain length (MCL) 3-hydroxyalkanoate-lactate terpolymer (poly(3-hydroxybutyrate-co-MCL 3-hydroxyalkanoate-co-lactate)), 3-hydroxybutyrate-3-hydroxyvalerate-lactate terpolymer (poly(3-hydroxybutyrate-co-3-hydroxyvalerate-co-lactate)), 3-hydroxypropionate-lactate copolymer (poly(3-hydroxypropionate-co-lactate)) and 3-hydroxybutyrate-3-hydroxypropionate-lactate terpolymer (poly(3-hydroxybutyrate-co-hydroxypropionate-co-lactate)) as the copolymer.

The present invention also provides a method for preparing a copolymer comprising lactate monomer unit and 3-hydroxyalkanoate monomer unit, wherein the method comprises culturing a cell or plant comprising a gene of enzyme converting lactate into lactyl-CoA and converting 3-hydroxyalkanoate into 3-hydroxyalkanoyl-CoA and polyhydroxyalkanoate (PHA) synthase gene together.

In the present invention, the cell or plant can be obtained by transforming a cell or plant not having any one or both of the two enzymes with a gene of enzyme converting lactate and 3-hydroxyalkanoate into lactyl-CoA and 3-hydroxyalkanoyl-CoA, respectively, and/or a gene of PHA synthase using lactyl-CoA as a substrate.

More preferably, in the present invention, the gene of enzyme converting lactate and 3-hydroxyalkanoate into lactyl-CoA and 3-hydroxyalkanoyl-CoA, respectively, is propionyl-CoA transferase gene (pct).

In the present invention, the cell or plant can further comprise a gene of enzyme converting 3-hydroxyalkanoate into 3-hydroxyalkanoyl-CoA, and the enzyme converting hydroxyalkanoate into 3-hydroxyalkanoyl-CoA is alpha-ketothiolase (PhaA) and/or acetoacetyl-CoA reductase (PhaB).

Preferably, in the preparing method according to the present invention, the cell is preferably a microorganism. More preferably, and more preferably, the microorganism is *E. Coli*.

In the present invention, the culturing is performed in a medium comprising 3-hydroxyalkanoate, and the 3-hydroxyalkanoate can be at least one selected from the group consisting of 3-hydroxybutyrate, 3-hydroxyvalerate, 3-hydroxypropionate and medium chain length (MCL) 3-hydroxyalkanoate. In addition, valeric acid, propionic acid, etc. can be used as sources of 3-hydroxyvalerate, 3-hydroxypropionate, etc.

The cell or plant being able to synthesize the copolymer comprising 3-hydroxyalkanoate monomer unit and lactate monomer unit can be obtained by (i) transforming a cell or plant not having the two enzymes with a gene of enzyme converting lactate and 3-hydroxyalkanoate into lactyl-CoA and 3-hydroxyalkanoyl-CoA, respectively, and a gene of PHA synthase using lactyl-CoA as a substrate, (ii) transforming a cell or plant having a gene of PHA synthase using lactyl-CoA as a substrate with a gene of enzyme converting lactate and 3-hydroxyalkanoate into lactyl-CoA and 3-hydroxyalkanoyl-CoA, respectively, or (iii) transforming a cell or plant having a gene of enzyme converting lactate and 3-hydroxyalkanoate into lactyl-CoA and 3-hydroxyalkanoyl-CoA, respectively, with a gene of PHA synthase using lactyl-CoA as a substrate. However, the scope of the present invention is not limited to the concrete examples described above.

The cell or plant having a gene of enzyme converting lactate and 3-hydroxyalkanoate into lactyl-CoA and 3-hydroxyalkanoyl-CoA, respectively, a PHA synthase gene, and a gene of enzyme converting 3-hydroxyalkanoate into 3-hydroxyalkanoyl-CoA together can be obtained by (i) transforming a cell or plant having a gene of enzyme converting lactate and 3-hydroxyalkanoate into lactyl-CoA and 3-hydroxyalkanoyl-CoA, respectively, with a gene of PHA synthase using lactyl-CoA as a substrate and a gene of enzyme converting 3-hydroxyalkanoate into 3-hydroxyalkanoyl-CoA, (ii) transforming a cell or plant having a gene of PHA synthase using lactyl-CoA as a substrate with a gene of enzyme converting lactate and 3-hydroxyalkanoate into lactyl-CoA and 3-hydroxyalkanoyl-CoA, respectively, and a gene converting into 3-hydroxyalkanoyl-CoA, (iii) transforming a cell or plant having a gene of enzyme converting 3-hydroxyalkanoate into 3-hydroxyalkanoyl-CoA with a gene of enzyme converting lactate and 3-hydroxyalkanoate into lactyl-CoA and 3-hydroxyalkanoyl-CoA, respectively, and a gene of PHA synthase using lactyl-CoA as a substrate, (iv) transforming a cell or plant having a gene of enzyme converting lactate and 3-hydroxyalkanoate into lactyl-CoA and 3-hydroxyalkanoyl-CoA, respectively, and a gene of PHA synthase using lactyl-CoA as a substrate with a gene of enzyme converting 3-hydroxyalkanoate into 3-hydroxyalkanoyl-CoA, (v) transforming a cell or plant having a gene of enzyme converting 3-hydroxyalkanoate into 3-hydroxyalkanoyl-CoA and a gene of PHA synthase using lactyl-CoA as a substrate with a gene of enzyme converting lactate and 3-hydroxyalkanoate into lactyl-CoA and 3-hydroxyalkanoyl-CoA, respectively, or (vi) transforming a cell or plant having a gene of enzyme converting 3-hydroxyalkanoate into 3-hydroxyalkanoyl-CoA and a gene of enzyme converting lactate and 3-hydroxyalkanoate into lactyl-CoA and 3-hydroxyalkanoyl-CoA, respectively, with a gene of PHA synthase using lactyl-CoA as a substrate. However, the scope of the present invention is not limited to the concrete examples described above.

In the present invention, the 3-hydroxyalkanoate is preferably at least one selected from the group consisting of 3-hydroxybutyrate, 3-hydroxyvalerate, 3-hydroxy-propionate and MCL 3-hydroxyalkanoate, and the MCL 3-hydroxyalkanoate is preferably hydroxyalkanoate having 6-12 carbon numbers. More specifically, the MCL 3-hydroxyalkanoate is preferably 3-hydroxyhexanoate (3HHx), 3-hydroxyheptanoate (3HHp), 3-hydroxyoctanoate (3HO), 3-hydrononanoate (3HN), 3-hydroxydecanoate (3HD), 3-hydroxyundecanoate (3HUD), 3-hydroxydodecanoate (3HDD) or their mixture.

Furthermore, the cells or plants may be transformed with a recombinant vector comprising pct gene. At the same time, the cells or plants may be transformed with a vector comprising phaC, or phaC is inserted into a chromosome. In addition, in case that a gene encoding PHA synthase for which lactyl-CoA is a substrate is phaC, the cells or plants may be transformed with a recombinant vector comprising pct gene. At the same time, the cells or plants may be transformed with a vector comprising phaC, or phaC is inserted into a chromosome.

As is known in the art, various microorganisms have a gene encoding PHA synthase (Korea Patent issued No. 10-250830). The following are examples of such microorganisms: microorganisms of the genus *Achromobacter* that include *Achromobacter* sp., *Achromobacter xylosoxidans*, etc., microorganisms of the genus *Acinetobacter* that include *Acidovorax delafieldii*, *Acidovax facilis*, *Acinetobacter* sp., *Acinetobacter calcoaceticus*, *Acinetobacter lwoffii*, etc., microorganisms of the genus *Aeromonas* that include *Actinomyces* sp., *Aeromonas caviae*, *Aeromonas hydrophila*, *Aeromonas salmonicida*, etc., microorganisms of the genus *Alcaligenes* that include *Alcaligenes aestus*, *Alcaligenes denitrificans*, *Alcaligenes eutrophus* (after renamed as *Ralstonia eutropha*, it is renamed as *Wautersia eutropha*), *Alcaligenes faecalis*, *Alcaligenes latus*, *Alcaligenes pacificus*, *Alcaligenes paradoxus*, *Alcaligenes venestus*, etc., microorganisms of the genus *Amoebobacter* that include *Alteromonas macleodii*, *Amoebobacter rosea*, *Amoebobacter pendens*, etc., microorganisms of the genus *Azospirillum* that include

*Aphanocapa* sp., *Aphanothece* sp., *Aquaspirillum autotrophicum, Azorhizobium caulinodans, Azospirillum* sp., *Azospirillum brasilense, Azospirillum lipoferum*, etc., microorganisms of the genus *Azotobacter* that include *Azotobacter* sp., *Azotobacter agilis, Azotobacter chroococcum, Azotobacter macrocytogenes, Azotobacter vinelandii*, etc., microorganisms of the genus *Bacillus* that include *Bacillus anthracis, Bacillus cereus, Bacillus megaterium, Bacillus subtillus, Bacillus thuringiensis*, etc., microorganisms of the genus *Beggiatoa* that include *Beggiatoa* sp., *Beggiatoa alba*, etc., microorganisms of the genus *Beijerinckia* that include *Beijerinckia indicus, Beijerinckia mobilis*, etc., microorganisms of the genus *Beneckea* that include *Beneckea natrigens, Beneckea pelagia*, etc., microorganisms of the genus *Caulobacter* that include *Bordetella pertussis, Bradyrhizobium japonicum, Caryophamon latum, Caulobacter bacteroides, Caulobacter crescentus*, etc., microorganisms of the genus *Chlorogloea* that include *Chloroflexus aurantiacus, Chlorogloea fritschii*, etc., microorganisms of the genus *Chromatium* that include *Chromatium minutissimum, Chromatium okenii, Chromatium tepidum*, etc., microorganisms of the genus *Chromobacterium* that include *Chromobacterium violaceum*, etc., microorganisms of the genus *Clostridium* that include *Clostridium botulinum, Clostridium sphenoides*, etc., microorganisms of the genus *Comamonas* that include *Comamonas acidovorans, Comamonas testosteroni*, etc., microorganisms of the genus *Corynebacterium* that include *Corynebacterium autotrophicum, Corynebacterium hydrocarboxydans*, etc., microorganisms of the genus *Derxia* that include *Cyanobacteria, Derxia gummosa*, etc., microorganisms of the genus *Desulfonema* that include *Desulfococcus multivorans, Desulfonema limicola, Desulfonema magnum*, etc., microorganisms of the genus *Ectothiorhodospira* that include *Desulfosacina variabilis, Desulfovibrio sapovorans, Ectothiorhodospira halochloris, Ectothiorhodospira mobilis, Ectothiorhodospira vacuolata*, etc., microorganisms of the genus *Halobacterium* that include *Ferrobacillus ferroxidans, Flavobacterium* sp., *Haemophilus influenzae, Halobacterium gibbonsii, Halobacterium volcanii*, etc., microorganisms of the genus *Hydrogenophaga* that include *Haloferax mediterranei, Hydroclathratus clathratus, Hydrogenomonas facilis, Hydrogenophaga flava, Hydrogenophaga pseudoflava, Hydrogenophaga taeniospiralis*, etc., microorganisms of the genus *Hyphomicrobium* that include *Hyphomicrobium vulgare*, etc., microorganisms of the genus *Methylbacterium* that include *Ilyobater delafieldii, Labrys monachus, Lamprocystis reseopersicina, Lampropedia hyaline, Legionella* sp., *Leptothrix discophorus, Methylbacterium AM1, Methylbacterium extorquens*, etc., microorganisms of the genus *Methylosinus* that include *Methylococcus thermophilus, Methlocystis parvus, Methylomonas methanica, Methylosinus sporium, Methylosinus trichosporium*, etc., microorganisms of the genus *Micrococcus* that include *Methylovibrio soehngenii, Micrococcus denitrificans, Micrococcus halodenitrificans*, etc., microorganisms of the genus *Mycobacterium* that include *Mycobacterium album, Mycobacterium vacae*, etc., microorganisms of the genus *Nitrobacter* that include *Nitrobacter agilis, Nitrobacter winogradskyi*, etc., microorganisms of the genus *Nocardia* that include *Nocardia alba, Nocardia asteroides, Nocardia lucida, Nocardia rubra*, etc., microorganisms of the genus *Photobacterium* that include *Paracoccus dentrificans, Oscillatoria limosa, Penicillium cyclopium, Photobacterium mandapamensis, Photobacterium phosphoreum*, etc., microorganisms of the genus *Pseudomonas* that include *Physarum ploycephalum* and *Pseudomonas glathei, Pseudomonas indigofera, Pseudomonas lemonieri, Pseudomonas mallei, Pseudomonas marina, Pseudomonas mixta, Pseudomonas oleovorans, Pseudomonas oxalaticus, Pseudomonas pseudoalcaligenes, Pseudomonas aeruginosa, Pseudomonas alcaligenes, Pseudomonas asplenii, Pseudomonas butanovora, Pseudomonas cepacia, Pseudomonas coronafaciens, Pseudomonas dacunhae, Pseudomonas denitrificans, Pseudomonas diminuta, Pseudomonas echinoides, Pseudomonas fluorescens, Pseudomonas putida, Pseudomonas rubrilineas, Pseudomonas saccharophila, Pseudomonas stutzeri, Pseudomonas syringae, Pseudomonas thermophilus, Pseudomonas viridiflava*, etc., microorganisms of the genus *Ralstonia*, microorganisms of the genus *Rhizobium* that include *Rhizobium hedysarum, Rhizobium lupini, Rhizobium meliloti, Rhizobium phaseoli, Rhizobium trifoli*, etc., microorganisms of the genus *Rhodobacillus*, microorganisms of the genus *Rhodobacter* that include *Rhodobacter capsulatus, Rhodobacter sphaeroides*, etc., microorganisms of the genus *Rhodococcus* that include *Rhodococcus rhodochrous*, etc., microorganisms of the genus *Rhodocyclus* that include *Rhodocyclus gelatinosus, Rhodocyclus tenuis*, etc., microorganisms of the genus *Rhodopseudomonas* that include *Rhodomicrobium vannielii* and *Rhodopseudomonas acidophile, Rhodopseudomonas capsulata*, etc., microorganisms of the genus *Rhodospirillum* that include *Rhodospirillum molischianum, Rhodospirillum rubrum*, etc., microorganisms of the genus *Spirillum* that include *Sphingomonas paucimobilis, Spirillum itersomii, Spirillum serpens*, etc., microorganisms of the genus *Spirulina* that include *Spirulina jenneri, Spirulina maxima, Spirulina subsaksa*, etc., microorganisms of the genus *Staphylococcus* that include *Staphylococcus aureus, Staphylococcus epidermidis, Staphylococcus xylosus*, etc., microorganisms of the genus *Stella* that include *Stella humosa, Stella vacuolata*, etc., microorganisms of the genus *Streptomyces* that include *Streptomyces antibioticus, Streptomyces coelicolor*, etc., microorganisms of the genus *Thiobacillus* that include *Syntrophomonas wolfei, Thermophilic cyanobacteria, Thermus thermophilus, Thiobacillus A2, Thiobacillus acidophilus, Thiobacillus versutus*, etc., microorganisms of the genus *Thiocapsa* that include *Thiocapsa pfennigii*, etc., microorganisms of the genus *Zoogloea* that include *Thiocystis violacea, Vibrio parahaemolyticus, Xanthobacter autotrophicus, Xanthomonas maltophilia, Zoogloea ramigera*, etc.

Preferably, the polyhydroxyalkanoate (PHA) synthase gene of the present invention is phaC1$_{ps6-19}$ originated from *Pseudomonas* sp. 6-19. More preferably, the PHA synthase gene encodes the amino acid sequence of SEQ ID NO: 8 having mutations of: a) S325T and Q481M; b) 5130D and Q481K; c) S325T and Q481K; d) E130D and Q481M; e) E130D and Q481R; f) E130D, S325T and Q481M; g) E130D, S325T and Q481K; h) E130D, S477R and Q481K; i) E130D, S477R and Q481M; j) E130D, S477R and Q481R; k) E130D, S477H and Q481K; 1) E130D, S477H and Q481M; m) E130D, S477H and Q481R; n) E130D, S477F and Q481K; o) E130D, S477F and Q481M; p) E130D, S477F and Q481R; q) E130D, S477Y and Q481K; r) E130D, S477Y and Q481M; s) E130D, S477Y and Q481R; t) E130D, S325T, S477R and Q481M; u) E130D, S325T, S477R and Q481K; v) E130D, S325T, S477F and Q481M; w) E130D, S325T, S477G and Q481M; or x) E130D, S325T, S477F and Q481K. These PHA synthase mutants are more preferable in aspect of using lactyl-CoA as a substrate.

In the present invention, the cell or plant having the gene of enzyme converting lactate and 3-hydroxyalkanoate into lactyl-CoA and 3-hydroxyalkanoyl-CoA, respectively, and polyhydroxyalkanoate (PHA) synthase gene together can be cultured in a medium comprising 3-hydroxyalkanoate to produce the copolymer of the present invention. If the cell or plant can biosynthesize lactate and 3-hydroxyalkanoate from other carbon sources such as glucose, citric acid, etc., there may be no need to further add 3-hydroxyalkanoate, lactate and so on to the medium.

Transformation of plants for preparing plant comprising genes of transferase and synthase can be achieved by conventional methods using *Agrobacterium* or virus vectors. For example, transformed plants are obtained by transforming an *Agrobacterium* with a recombinant vector containing the inventive gene and infecting a tissue, etc. of the target plant with the transformed *Agrobacterium*. More specifically, the transformed plant can be prepared by pre-culturing an explant of plant of interest, and then transforming the explant by co-cultivating the explant and a transformed *Agrobactenium*; culturing said infected explants to induce callus; and excising obtained callus, and culturing it in shoot-inducing medium.

The term "explant," as used herein, means a tissue fragment cut from a plant, and includes cotyledon or hypocotyl. Cotyledon or hypocotyls can be used as the explant of the present invention. It is more preferable to use cotyledon obtained by disinfecting and washing seeds of the plant, and germinating it in MS medium.

Transformed plants useful for the present invention include, but are not limited to, tobacco, tomato, red peppers, beans, nice, and corn. Also, even though a transformed plant is one that propagates sexually, it will be obvious to a person skilled in the art that such a plant can be reproduced asexually using plant tissue culture, etc.

MODES FOR CARRYING OUT THE INVENTION

Hereinafter, the present invention is described in considerable detail. The following examples are offered by way of illustration to help those skilled in the art understand the present invention, and are not intended to limit the scope of the invention.

Example 1

Construction of a Recombinant Plasmid Comprising pct Gene and PHA Synthase Gene

Recombinant plasmids, pPs619C1300-CPPCT and pTac-CpPctNCvEC, comprising pct gene and PHA synthase gene were constructed to prepare a copolymer comprising 3-hydroxyalkanoate unit and lactate unit.

(1) Construction of Plasmid pPs619C1300-CPPCT

Pronpionyl-CoA transferase (CP-PCT) gene derived from *Clostridium propionicum* was used as the pct gene, and PHA synthase gene derived from *Pseudomonas* sp. 6-19 was used as the PHA synthase gene.

Figure 1:
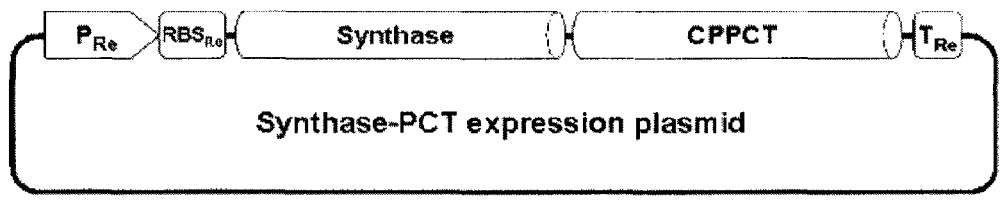
FIG. 1 is a simple diagram of constitutive expression operon system expressing PHA synthase and CP-PCT together.

The operon of constitutive expression system expressing PHA synthase and CP-PCT together was constructed like FIG. 1. CP-PCT was well known to have toxicity to host microorganism. That is, in tac promoter or T7 promoter expression system induced by IPTG (this system is widely used in expression of a recombinant protein); all microorganisms become dead shortly after the addition of inducer. Because of this reason, it is thought as suitable to use expression system in which it is weakly expressed, but continuously expressed according to the growth of microorganism. CP-PCT gene was obtained by PCR using the chromosome DNA of *Chostridium propionicum* (DSM1682) as template and the primers of SEQ ID NO: 1 and SEQ ID NO: 2 made based on pct gene sequence (Selmer et al., *Eur J. Biochem.*, 269:372, 2002).

SEQ ID NO: 1:
5-ggaattcATGAGAAAGGTTCCCATTATTACCGCAGATGA

SEQ ID NO: 2:
5-gctctagattaggacttcatttccttcagacccattaagccttctg

NdeI restriction enzyme site of wild CP-PCT was removed by SDM method for easiness of cloning. In addition, overlapping PCR was performed with the primers of SEQ ID NO: 3 and 4 to add SbfI/NdeI recognition site.

SEQ ID NO: 3:
5-agg cct gca ggc gga taa caa ttt cac aca gg-3

SEQ ID NO: 4:
5-gcc cat atg tct aga tta gga ctt cat ttc c-3

To separate the gene of PHA synthase (phaC1$_{Ps6-19}$) originated from *Pseudomonas* sp. 6-19 (KCTC 11027BP), total DNA of *Pseudomonas* sp. 6-19 was extracted, and the primers of SEQ ID NO: 5 and 6 were prepared based on the sequence of phaC1$_{Ps6-19}$ gene (Ae-jin Song, Master's Thesis, Department of Chemical and Biomolecular Engineering, KAIST, 2004) and PCR was performed to get the gene of phaC1$_{Ps6-19}$. The nucleotide sequence of phaC1$_{Ps6-19}$ gene is shown in SEQ ID NO: 7, from which the amino acid sequence evaluated is shown in SEQ ID NO: 8.

SEQ ID NO: 5:
5-GAG AGA CAA TCA AAT CAT GAG TAA CAA GAG TAA CG-3

SEQ ID NO: 6:
5-CAC TCA TGC AAG CGT CAC CGT TCG TGC ACG TAC-3

The above obtained phaC1$_{Ps6-19}$ gene was inserted into BstBI/SbfI site of pBluescript II (Stratagene Co., USA) to make pPs619C1 recombinant vector. BstBI sites contained inside were removed by SDM (site directed mutagenesis) method without mutation of amino acid to make phaC1$_{Ps6-19}$ synthase gene fragment having two BstBI/SbfI sites only at the both ends, and overlapping PCR were performed with the primers of SEQ ID NO: 9 and 10, SEQ ID NO: 11 and 12, and SEQ ID NO: 13 and 14 to add BstBI/SbfI-recognition site.

SEQ ID NO: 9:
5-atg ccc gga gcc ggt tcg aa-3

SEQ ID NO: 10:
5-CGT TAC TCT TGT TAC TCA TGA TTT GAT TGT CTC TC-3

SEQ ID NO: 11:
5-GAG AGA CAA TCA AAT CAT GAG TAA CAA GAG TAA CG-3

SEQ ID NO: 12:
5-CAC TCA TGC AAG CGT CAC CGT TCG TGC ACG TAC-3

SEQ ID NO: 13:
5-GTA CGT GCA CGA ACG GTG ACG CTT GCA TGA GTG-3

SEQ ID NO: 14: 5-aac ggg agg gaa cct gca gg-3

Three positions (130, 325, and 481) of amino acid affecting SCL (short-chain-length PHA) synthesis activity of phaC1$_{Ps6-19}$ synthase were found out through amino acid sequence alignment analysis, and pPs619C1300 comprising the gene encoding the mutant having mutations of E130D, S325T and Q481M in the amino acid sequence phaC1$_{Ps6-19}$ synthase was constructed by SDM method using the primer of SEQ ID NO: 15/16, 17/18 and 19/20 (FIG. 1). The phaC1$_{Ps6-19}$ synthase mutant was shown in table 1 below.

TABLE 1

| Recombinant vector | Necleic acid substitution | Amino acid substitution | Primer |
|---|---|---|---|
| pPs619C1300 | GAA →GAT | E130D | SEQ ID NO: 15/16 |
|  | AGC →ACC | S325T | SEQ ID NO: 17/18 |
|  | CAG →ATG | Q481M | SEQ ID NO: 19/20 |

SEQ ID NO: 15: 5-atc aac ctc atg acc gat gcg atg gcg ccg acc-3
SEQ ID NO: 16: 5-ggt cgg cgc cat cgc atc ggt cat gag gtt gat-3
SEQ ID NO: 17: 5-CTG ACC TTG CTG GTG ACC GTG CTT GAT ACC ACC-3
SEQ ID NO: 18: 5-GGT GGT ATC AAG CAC GGT CAC CAG CAA GGT CAG-3
SEQ ID NO: 19: 5-CGA GCA GCG GGC ATA TC A TGA GCA TCC TGA ACC CGC-3
SEQ ID NO: 20: 5-GCG GGT TCA GGA TGC TCA TGA TAT GCC CGC TGC TCG-3

Figure 2:
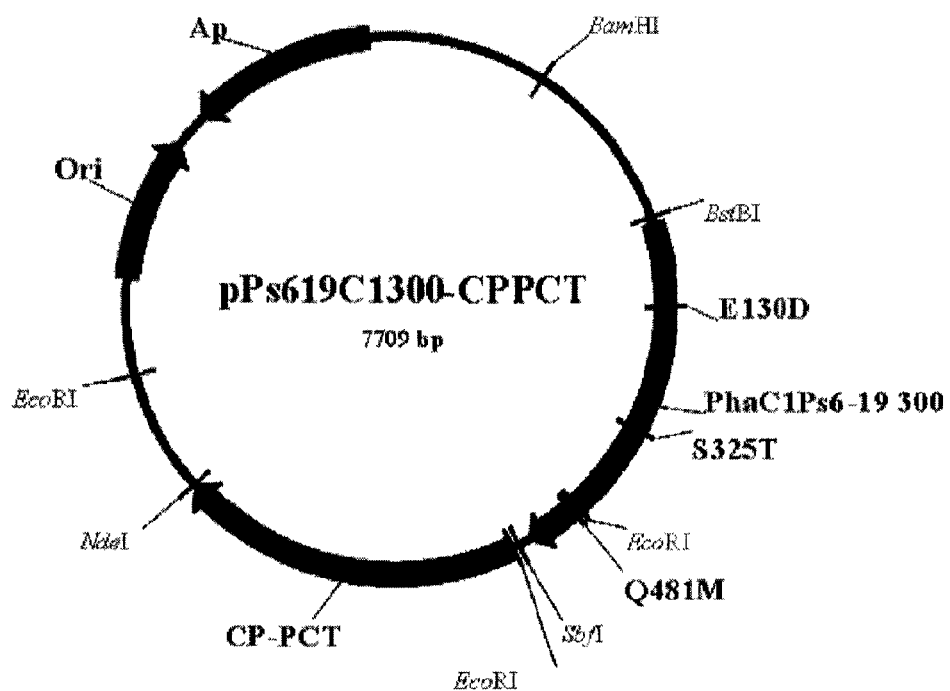
FIG. 2 is a gene map of recombinant plasmid pPs619C1300-CPPCT comprising PHA synthase gene and CP-PCT gene according to the present invention.

The obtained pPs619C1300 vector was excised with SbfI/NdeI, and the cloned CP-PCT gene was inserted into SbfI/NdeI recognition site to construct the pPs619C1300-CPPCT recombinant vector (FIG. 2).

(2) Construction of pMCS104ReAB

Figure 4:
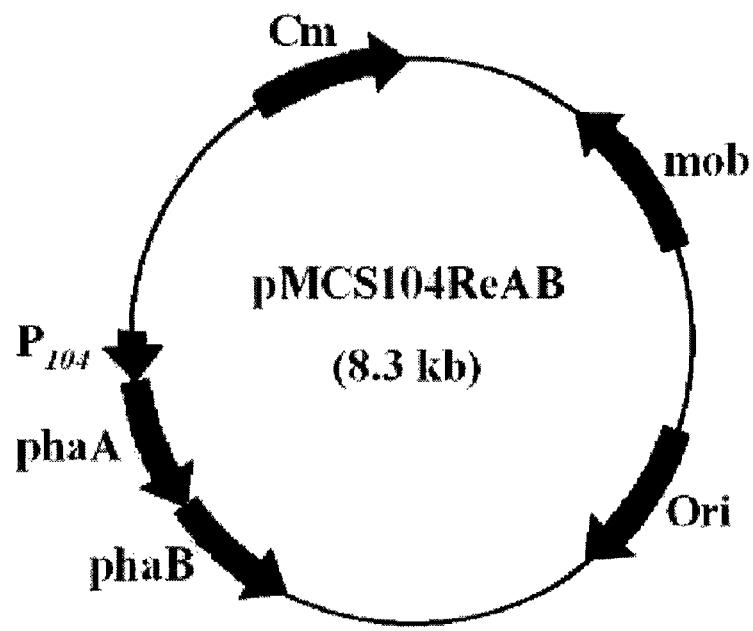
FIG. 4 is a gene map of recombinant plasmid pMCS104ReAB comprising phaA and phaB genes of *Ralstonia eutropha*.

Plasmid pMCS104ReAB was constructed to provide alpha-ketothiolase (PhaA) and acetoacetyl-CoA reductase (PhaB) derived from *R. eutropha* (Si-Jae Park, PhD thesis, Department of Chemical and Biomolecular Engineering, KAIST, 2003). pSYL105 (Lee et al. *Biotechnol. Bioeng.* 44: 1337, 1994) was cut with PstI to get phaAB gene, which was inserted into PstI-cut site of p10499A (Park et al., *FEMS Microbiol. Lett.*, 214:217, 2002) to construct p10499PhaAB. The p10499PhaAB plasmid was cut with SspI to get a fragment comprising 104 promoter and phaAB gene, and the fragment was inserted into EcoRV-cut site of pBBR1MCS plasmid to obtain pMCS104ReAB plasmid (FIG. 4).

(3) Construction of pTacCpPctNCvEC Plasmid pTac99A vector (Park and Lee, *J. Bacteriol.* 185, 5391-5397, 2003) was cut with SspI to get a gene fragment comprising Tac promoter and transcription terminator, and the fragment was inserted into pTrc99A (Pharmacia Biotech, Sweden) exercised with restriction enzyme SspI to make pTaclac vector. phaEC gene was amplified with the chromosome DNA of *Chromatium vinosum* (DSMZ180) as template and the primers of SEQ ID NO: 21 and 22.

SEQ ID NO: 21:
ggaaatc cat ATGACGATGTTCTCGCTCATGGCG

SEQ ID NO: 22:
ggaaatc catatg atc cag ggc cac tat ctc caa ctg

Figure 3:
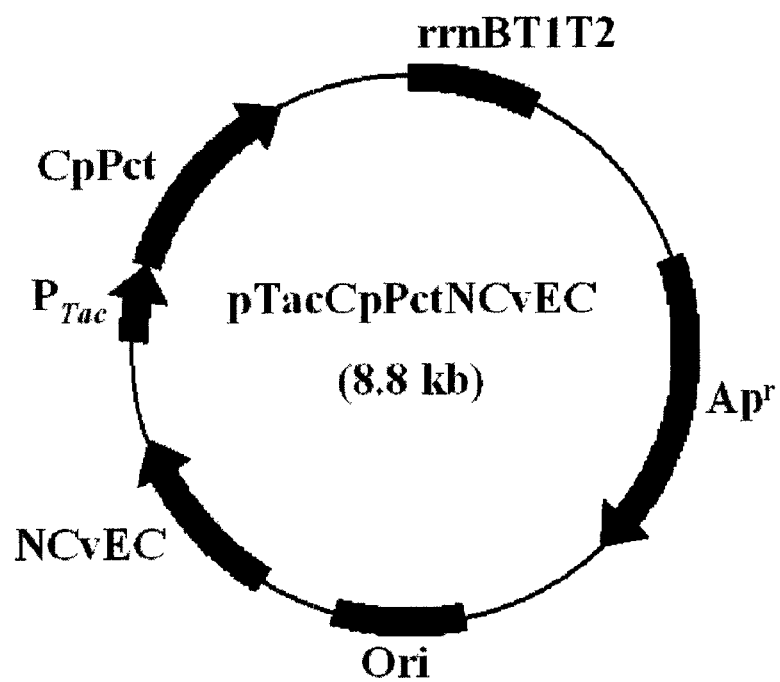
FIG. 3 is a gene map of recombinant plasmid pTacCpPct-NCvEC comprising PHA synthase gene and CP-PCT gene according to the present invention.

The amplified phaEC gene was inserted into the NdeI-excised site of the pTaclac vector to make pTaclacNCvEC vector. In addition, pct gene was obtained by cutting pPs619C1300-CPPCT with EcoRI/XbaI, and the pct gene was inserted into the EcoRI/XbaI-cut site of pTaclacNCvEC to make pTacCpPctNCvEC (FIG. 3).

Example 2

Preparation of MCL 3-hydroxyalkanoate-lactate Copolymer

*E. coli* WB101 (Park and Lee, J. Bacteriol. 185, 5391-5397, 2003) was transformed with the recombinant plasmid pPs619C1300-CPPCT constructed in the example 1, comprising pct gene and PHA synthase gene to obtain *E. coli* WB101/pPs619C1300-CPPCT. WB101 is reported to be a fadB *E. Coli* mutant that is effective in preparing MCL-PHA (Korea Patent Issued No. 10-0447531).

The transformant was cultured by two steps to get MCL 3-hydroxyalkanoate-lactate copolymer as follows: First, the transformed recombinant *E. coli* WB101/pPs619C1300-CPPCT was cultured for 24 hours in 100 mL of LB medium (Bacto™ Triptone(BD) 10 g/L, Bacto™ yeast extract (BD) 5 g/L; NaCl (amresco) 10 g/L) containing 100 mg/L of ampicillin, and then the medium was centrifuged for 15 minutes at 4° C., 1000 g to collect cells.

Collected cells was anaerobically cultured for 3 days in LB medium (Bacto™ Triptone (BD) 10 g/L, Bacto™ yeast extract (BD) 5 g/L; NaCl (amresco) 10 g/L) further comprising 10 g/L of glucose, 2 g/L of sodium decanoate and 100 mg/L of ampicillin.

The culture medium was centrifuged for 15 minutes at 4° C., 1000 to collect cells, and the cells was washed 4 times with lots of distilled water and dried for 12 hours at 80° C. Completely dried cells was quantified, and reacted with methanol at 100° C. in chloroform solvent under the catalyst of sulfuric acid. Half volume of distilled water was added at room temperature to the chloroform, and mixed. Then, the mixture was settled until separated into two layers. In two layers, the chloroform layer dissolving methylated monomer was collected, and the ingredients of the polymer were analyzed with gas chromatography. Benzoate was used as internal standard.

As a result of the analysis, methyl-3-hydrodecanoate and methyl-lactate were detected in *E. coli* WB101/pPs619C1300-CPPCT transformant, which meant that MCL 3-hydroxyalkanoate-lactate copolymer [poly(MCL 3-hydroxyalkanoate-co-lactate)] was prepared by the recombinant *E. Coli*.

Example 3

Preparation of 3-hydroxybutyrate-MCL 3-hydroxyalkanoate-lactate terpolymer

*E. coli* WB101 [W3110(fadB::Km), Park and Lee, *J. Bacteriol.* 185:5391, 2003] was transformed with the recombinant plasmid pPs619C1300-CPPCT constructed in the example 1, comprising pct gene and PHA synthase gene to obtain *E. coli* WB101/pPs619C1300-CPPCT. WB101 is reported to be a fadB E. Coli mutant that is effective in preparing MCL-PHA (Korea Patent Issued No. 10-0447531).

The transformant was cultured by two steps to get 3-hydroxybutyrate-MCL 3-hydroxyalkanoate-lactate terpolymer as follows: First, the transformed recombinant E. coli WB101/pPs619C1300-CPPCT was cultured for 24 hours in 100 mL of LB medium (Bacto™ Triptone(BD) 10 g/L, Bacto™ yeast extract (BD) 5 g/L; NaCl (amresco) 10 g/L) containing 100 mg/L of ampicillin, and then the medium was centrifuged for 15 minutes at 4° C., 1000 g to collect cells.

Collected cells was anaerobically cultured for 3 days in LB medium (Bacto™ Triptone (BD) 10 g/L, Bacto™ yeast extract (BD) 5 g/L; NaCl (amresco) 10 g/L) further comprising 1 g/L of 3-hydroxybutyrate, 2 g/L of sodium decanoate and 100 mg/L of ampicillin.

In addition, E. coli WB101 was transformed with pPs619C1300-CPPCT and pMCS104ReAB to get E. coli WB101/pPs619C1300-CPPCT/pMCS104ReAB.

The E. coli WB101/pPs619C1300-CPPCT/pMCS104ReAB was cultured by two steps to get 3-hydroxybutyrate-3-hydroxyvalerate-lactate terpolymer as follows: First, the transformed recombinant E. coli WB101/pPs619C1300-CPPCT/pMCS104ReAB was cultured for 24 hours in 100 mL of LB medium (Bacto™ Triptone(BD) 10 g/L, Bacto™ yeast extract (BD) 5 g/L; NaCl (amresco) 10 g/L) containing 100 mg/L of ampicillin and 30 mg/L of chloramphenicol, and then the medium was centrifuged for 15 minutes at 4° C., 1000 g to collect cells. Collected cells was anaerobically cultured for 3 days in LB medium further comprising 1 g/L of 3-hydroxybutyrate, 2 g/L of sodium decanoate and 100 mg/L of ampicillin.

The culture media of E. coli WB101/pPs619C1300-CPPCT and E. coli WB101/pPs619C1300-CPPCT/pMCS104ReAB were centrifuged for 15 minutes at 4° C., 1000 to collect cells, and the cells were washed 4 times with lots of distilled water and dried for 12 hours at 80° C. Completely dried cells were quantified, and reacted with methanol at 100° C. in chloroform solvent under the catalyst of sulfuric acid. Half volumes of distilled water were added at room temperature to the chloroforms, and mixed. Then, the mixtures were settled until separated into two layers. In two layers, the chloroform layers dissolving methylated monomer were collected, and the ingredients of the polymer were analyzed with gas chromatography. Benzoate was used as internal standard.

Figure 5:
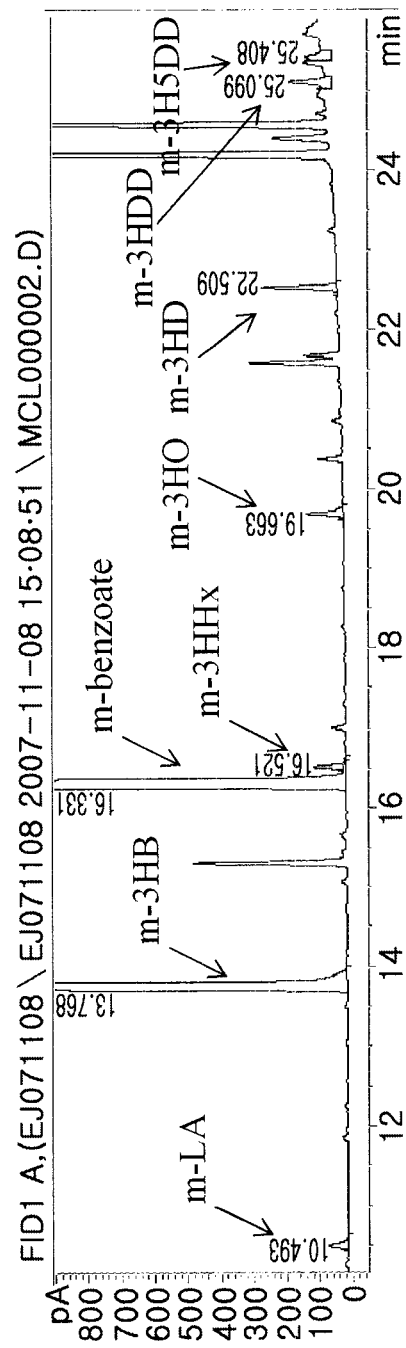
FIG. 5 is a gas chromatography result of P(3HB-co-MCL PHA-co-LA) terpolymer prepared by the recombinant *E. Coli* transformed with pPs619C1300-CPPCT/pMCS104ReAB plasmid.

As a result of the analysis, methyl-3-hydroxybutyrate, methyl-3-hydroxydecanoate and methyl-lactate were detected in E. coli WB101/pPs619C1300-CPPCT and E. coli WB101/pPs619C1300-CPPCT/pMCS104ReAB transformants, which meant that 3-hydroxybutyrate-MCL 3-hydroxyalkanoate-lactate terpolymer [poly(3-hydroxybutyrate-co-MCL 3-hydroxyalkanoate-co-lactate)] was prepared by those recombinant E. Coli (FIG. 5).

Example 4

Preparation of 3-hydroxybutyrate-3-hydroxyvalerate-lactate copolymer

E. coli Top 10 (Invitrogen) was transformed with the recombinant plasmid pPs619C1300-CPPCT constructed in the example 1, comprising pct gene and PHA synthase gene to obtain E. coli Top10/pPs619C1300-CPPCT.

The transformant was cultured by two steps to get 3-hydroxybutyrate-3-hydroxyvalerate-lactate terpolymer as follows: First, the transformed recombinant E. coli Top10/pPs619C1300-CPPCT was cultured for 24 hours in 100 mL of LB medium (Bacto™ Triptone(BD) 10 g/L, Bacto™ yeast extract (BD) 5 g/L; NaCl (amresco) 10 g/L) containing 100 mg/L of ampicillin, and then the medium was centrifuged for 15 minutes at 4° C., 1000 g to collect cells.

Collected cells was anaerobically cultured for 3 days in MR medium (Glucose 10 g, $KH_2PO_4$ 6.67 g, $(NH_4)_2HPO_4$ 4 g, $MgSO_4.7H_2O$ 0.8 g, citric acid 0.8 g and trace metal solution 5 mL per 1 L; Trace metal solution composition: 5M HCl 5 mL, $FeSO_4.7H_2O$ 10 g, $CaCl_2$ 2 g, $ZnSO_4.7H_2O$ 2.2 g, $MnSO_4.4H_2O$ 0.5 g, $CuSO_4.5H_2O$ 1 g, $(NH_4)_6Mo_7O_2.4H_2O$ 0.1 g, and $Na_2B_4O_2.10H_2O$ 0.02 g per 1 L) further comprising 1 g/L of 3-hydroxyvalerate (3-HV), 1 g/L of 3-hydroxybutyrate (3-HB) and 100 mg/L of ampicillin.

In addition, E. coli Top 10 (Invitrogen) was transformed with both pPs619C1300-CPPCT and pMCS104ReAB to get E. coli Top10/pPs619C1300-CPPCT/pMCS104ReAB.

The transformant was cultured by two steps to get 3-hydroxybutyrate-3-hydroxyvalerate-lactate terpolymer as follows: First, the transformed recombinant E. coli Top10/pPs619C1300-CPPCT/pMCS104ReAB was cultured for 24 hours in 100 mL of LB medium (Bacto™ Triptone(BD) 10 g/L, Bacto™ yeast extract (BD) 5 g/L; NaCl (amresco) 10 g/L) containing 100 mg/L of ampicillin and 30 mg/L of chloramphenicol, and then the medium was centrifuged for 15 minutes at 4° C., 1000 g to collect cells.

Collected cells was anaerobically cultured for 3 days in MR medium (Glucose 10 g, $KH_2PO_4$ 6.67 g, $(NH_4)_2HPO_4$ 4 g, $MgSO_4.7H_2O$ 0.8 g, citric acid 0.8 g and trace metal solution 5 mL per 1 L; Trace metal solution composition: 5M HCl 5 mL, $FeSO_4.7H_2O$ 10 g, $CaCl_2$ 2 g, $ZnSO_4.7H_2O$ 2.2 g, $MnSO_4.4H_2O$ 0.5 g, $CuSO_4.5H_2O$ 1 g, $(NH_4)_6Mo_7O_2.4H_2O$ 0.1 g, and $Na_2B_4O_2.10H_2O$ 0.02 g per 1 L) further comprising 2 g/L of propionic acid or 2 g/L of valeric acid, and 100 mg/L of ampicillin and 30 mg/L of chloramphenicol.

The culture medium was centrifuged for 15 minutes at 4° C., 1000 to collect cells, and the cells was washed 4 times with lots of distilled water and dried for 12 hours at 80° C. Completely dried cells was quantified, and reacted with methanol at 100° C. in chloroform solvent under the catalyst of sulfuric acid. Half volume of distilled water was added at room temperature to the chloroform, and mixed. Then, the mixture was settled until separated into two layers. In two layers, the chloroform layer dissolving methylated monomer was collected, and the ingredients of the polymer were analyzed with gas chromatography. Benzoate was used as internal standard.

Figure 6:
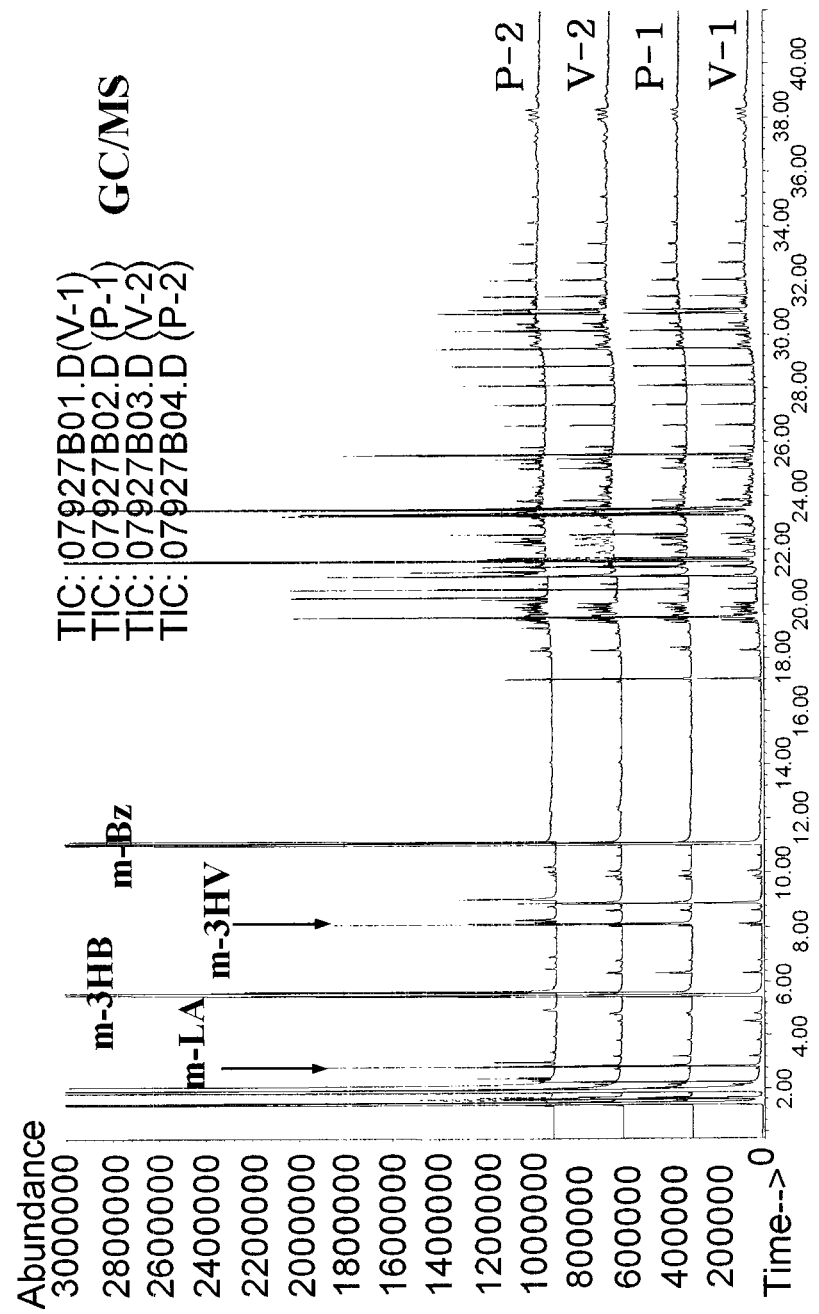
FIG. 6 is a gas chromatography result of P(3HB-co-3HV-co-LA) terpolymer prepared by the recombinant *E. Coli* transformed with pPs619C1300-CPPCT/pMCS104ReAB plasmid.

As a result of the analysis, methyl-3-hydroxybutyrate, metal-3-hydroxyvalerate and methyl-lactate were detected in both E. coli Top10/pPs619C1300-CPPCT and Top10/pPs619C1300-CPPCT/pMCS104ReAB, which meant that 3-hydroxybutyrate-3-hydroxyvalerate-lactate terpolymer [poly(3-hydroxybutyrate-co-3-hydroxyvalerate-co-lactate)] was prepared by the recombinant E. Coli (FIG. 6).

Example 5

Preparation of 3-hydroxypropionate-lactate Copolymer

E. coli Top 10 (Invitrogen) was transformed with the recombinant plasmid pPs619C1300-CPPCT constructed in the example 1, comprising pct gene and PHA synthase gene to obtain E. coli Top10/pPs619C1300-CPPCT.

The transformant was cultured by two steps to get 3-hydroxypropionate-lactate copolymer as follows: First, the transformed recombinant E. coli Top10/pPs619C1300-CPPCT was cultured for 24 hours in 100 mL of LB medium (Bacto™ Triptone(BD) 10 g/L, Bacto™ yeast extract (BD) 5 g/L; NaCl (amresco) 10 g/L) containing 100 mg/L of ampicillin, and then the medium was centrifuged for 15 minutes at 4° C., 1000 g to collect cells.

Collected cells were anaerobically cultured for 3 days in MR medium (Glucose 10 g, KH$_2$PO$_4$ 6.67 g, (NH$_4$)$_2$HPO$_4$ 4 g, MgSO$_4$.7H$_2$O 0.8 g, citric acid 0.8 g and trace metal solution 5 mL per 1 L; Trace metal solution composition: 5M HCl 5 mL, FeSO$_4$.7H$_2$O 10 g, CaCl$_2$ 2 g, ZnSO$_4$.7H$_2$O 2.2 g, MnSO$_4$.4H$_2$O 0.5 g, CuSO$_4$.5H$_2$O 1 g, (NH$_4$)$_6$Mo$_7$O$_2$.4H$_2$O 0.1 g, and Na$_2$B$_4$O$_2$.10H$_2$O 0.02 g per 1 L) further comprising 2 g/L of 3-hydropropionate (3-HP) and 100 mg/L of ampicillin.

The culture medium was centrifuged for 15 minutes at 4° C., 1000 to collect cells, and the cells were washed 4 times with lots of distilled water and dried for 12 hours at 80° C. Completely dried cells was quantified, and reacted with methanol at 100° C. in chloroform solvent under the catalyst of sulfuric acid. Half volume of distilled water was added at room temperature to the chloroform, and mixed. Then, the mixture was settled until separated into two layers. In two layers, the chloroform layer dissolving methylated monomer was collected, and the ingredients of the polymer were analyzed with gas chromatography. Benzoate was used as internal standard.

As a result of the analysis, methyl-3-hydroxypropionate and methyl-lactate were detected in *E. coli* Top10/pPs619C1300-CPPCT, which meant that new 3-hydroxypropionate-lactate copolymer [poly(3-hydroxypropionate-co-lactate)] was prepared by the recombinant *E. Coli*.

Example 6

Preparation of 3-hydroxybutyrate-3-hydroxypropionate-lactate Terpolymer

*E. coli* Top 10 (Invitrogen) was transformed with the recombinant plasmid pPs619C1300-CPPCT constructed in the example 1, comprising pct gene and PHA synthase gene to obtain *E. coli* Top10/pPs619C1300-CPPCT.

The transformant was cultured by two steps to get 3-hydroxybutyrate-3-hydroxypropionate-lactate terpolymer as follows: First, the transformed recombinant *E. coli* Top10/pPs619C1300-CPPCT was cultured for 24 hours in 100 mL of LB medium (Bacto™ Triptone(BD) 10 g/L, Bacto™ yeast extract (BD) 5 g/L; NaCl (amresco) 10 g/L) containing 100 mg/L of ampicillin, and then the medium was centrifuged for 15 minutes at 4° C., 1000 g to collect cells.

Collected cells were anaerobically cultured for 3 days in MR medium (Glucose 10 g, KH$_2$PO$_4$ 6.67 g, (NH$_4$)$_2$HPO$_4$ 4 g, MgSO$_4$.7H$_2$O 0.8 g, citric acid 0.8 g and trace metal solution 5 mL per 1 L; Trace metal solution composition: 5M HCl 5 mL, FeSO$_4$.7H$_2$O 10 g, CaCl$_2$ 2 g, ZnSO$_4$.7H$_2$O 2.2 g, MnSO$_4$.4H$_2$O 0.5 g, CuSO$_4$.5H$_2$O 1 g, (NH$_4$)$_6$Mo$_7$O$_2$.4H$_2$O 0.1 g, and Na$_2$B$_4$O$_2$.10H$_2$O 0.02 g per 1 L) further comprising 2 g/L of 3-hydroxypropionate (3-HP), 1 g/L of 3-hydroxybutyrate (3-HB) and 100 mg/L of ampicillin.

The culture medium was centrifuged for 15 minutes at 4° C., 1000 to collect cells, and the cells was washed 4 times with lots of distilled water and dried for 12 hours at 80° C. Completely dried cells was quantified, and reacted with methanol at 100° C. in chloroform solvent under the catalyst of sulfuric acid. Half volume of distilled water was added at room temperature to the chloroform, and mixed. Then, the mixture was settled until separated into two layers. In two layers, the chloroform layer dissolving methylated monomer was collected, and the ingredients of the polymer were analyzed with gas chromatography. Benzoate was used as internal standard.

As a result of the analysis, methyl-3-hydroxypropionate, methyl-3-hydroxybutyrate and methyl-lactate were detected in *E. coli* Top10/pPs619C1300-CPPCT, which meant that 3-hydroxybutyrate-3-propionate-lactate terpolymer [poly(3-hydroxybutyrate-co-hydroxypropionate-co-lactate)] was prepared by the recombinant *E. Coli*.

Example 7

Preparation of Various Mutants

Various PHA synthase mutants were prepared like the construction of the pPs619C1300 with the primers below. Obtained mutants were shown in tables 2, 3, 4 and 5.

```
E130D
SEQ ID NO: 15:
5'-atc aac ctc atg acc gat gcg atg gcg ccg acc-3'
SEQ ID NO: 16:
5'-ggt cgg cgc cat cgc atc ggt cat gag gtt gat-3'

S325T
SEQ ID NO: 17:
5'-CTG ACC TTG CTG GTG ACC GTG CTT GAT ACC ACC-3'
SEQ ID NO: 18:
5'-GGT GGT ATC AAG CAC GGT CAC CAG CAA GGT CAG-3'

S477R
SEQ ID NO: 23:
5'-gaa ttc gtg ctg tcg agc cgc ggg cat atc-3'
SEQ ID NO: 24:
5'-gat atg ccc gcg gct cga cag cac gaa ttc-3'

S477H
SEQ ID NO: 25:
5'-gaa ttc gtg ctg tcg agc cat ggg cat atc-3'
SEQ ID NO: 26:
5'-gat atg ccc atg gct cga cag cac gaa ttc-3'

S477F
SEQ ID NO: 27:
5'-gaa ttc gtg ctg tcg agc ttt ggg cat atc-3'
SEQ ID NO: 28:
5'-gat atg ccc aaa gct cga cag cac gaa ttc-3'

S477Y
SEQ ID NO: 29:
5'-gaa ttc gtg ctg tcg agc tat ggg cat atc-3'
SEQ ID NO: 30:
5'-gat atg ccc ata gct cga cag cac gaa ttc-3'

S477G
SEQ ID NO: 31:
5'-gaa ttc gtg ctg tcg agc ggc ggg cat atc-3'
SEQ ID NO: 32:
5'-gat atg ccc gcc gct cga cag cac gaa ttc-3'

Q481K
SEQ ID NO: 33:
5'-ggg cat atc aaa agc atc ctg aac ccg c-3'
SEQ ID NO: 34:
5'-gcg ggt tca gga tgc ttt tga tat gcc c-3'

Q481M
SEQ ID NO: 35:
5'-ggg cat atc atg agc atc ctg aac ccg c-3'
```

-continued

SEQ ID NO: 36:
5'-gcg ggt tca gga tgc tca tga tat gcc c-3'

Q481R
SEQ ID NO: 37:
5'-ggg cat atc cgc agc atc ctg aac ccg c-3'
SEQ ID NO: 38:
5'-gcg ggt tca gga tgc tgc gga tat gcc c-3'

TABLE 2

| Recombinant synthase | Nucleic acid substitution | Amino acid substitution | Primers |
|---|---|---|---|
| pPs619C1200 | AGC → ACC | S325T | SEQ ID NO: 17, 18 |
| | CAG → ATG | Q481M | SEQ ID NO: 35, 36 |
| pPs619C1202 | GAA → GAT | E130D | SEQ ID NO: 15, 16 |
| | CAG → AAA | Q481K | SEQ ID NO: 33, 34 |
| pPs619C1203 | AGC → ACC | S325T | SEQ ID NO: 17, 18 |
| | CAG → AAA | Q481K | SEQ ID NO: 33, 34 |
| pPs619C1204 | GAA → GAT | E130D | SEQ ID NO: 15, 16 |
| | CAG → ATG | Q481M | SEQ ID NO: 35, 36 |
| pPs619C1205 | GAA → GAT | E130D | SEQ ID NO: 15, 16 |
| | CAG → CGC | Q481R | SEQ ID NO: 37, 38 |

TABLE 3

| Recombinant synthase | Nucleic acid substitution | Amino acid substitution | Primers |
|---|---|---|---|
| pPs619C1300 | GAA → GAT | E130D | SEQ ID NO: 15, 16 |
| | AGC → ACC | S325T | SEQ ID NO: 17, 18 |
| | CAG → ATG | Q481M | SEQ ID NO: 35, 36 |
| pPs619C1301 | GAA → GAT | E130D | SEQ ID NO: 15, 16 |
| | AGC → ACC | S325T | SEQ ID NO: 17, 18 |
| | CAG → AAA | Q481K | SEQ ID NO: 33, 34 |
| pPs619C1304 | GAA → GAT | E130D | SEQ ID NO: 15, 16 |
| | AGC → CGC | S477R | SEQ ID NO: 23, 24 |
| | CAG → AAA | Q481K | SEQ ID NO: 33, 34 |
| pPs619C1305 | GAA → GAT | E130D | SEQ ID NO: 15, 16 |
| | AGC → CGC | S477R | SEQ ID NO: 23, 24 |
| | CAG → ATG | Q481M | SEQ ID NO: 35, 36 |
| pPs619C1306 | GAA → GAT | E130D | SEQ ID NO: 15, 16 |
| | AGC → CGC | S477R | SEQ ID NO: 23, 24 |
| | CAG → CGC | Q481R | SEQ ID NO: 37, 38 |
| pPs619C1307 | GAA → GAT | E130D | SEQ ID NO: 15, 16 |
| | AGC → CAT | S477H | SEQ ID NO: 25, 26 |
| | CAG → AAA | Q481K | SEQ ID NO: 33, 34 |
| pPs619C1308 | GAA → GAT | E130D | SEQ ID NO: 15, 16 |
| | AGC → CAT | S477H | SEQ ID NO: 25, 26 |
| | CAG → ATG | Q481M | SEQ ID NO: 35, 36 |
| pPs619C1309 | GAA → GAT | E130D | SEQ ID NO: 15, 16 |
| | AGC → CAT | S477H | SEQ ID NO: 25, 26 |
| | CAG → CGC | Q481R | SEQ ID NO: 37, 38 |
| pPs619C1310 | GAA → GAT | E130D | SEQ ID NO: 15, 16 |
| | AGC → TTT | S477F | SEQ ID NO: 27, 28 |
| | CAG → AAA | Q481K | SEQ ID NO: 33, 34 |

TABLE 4

| Recombinant synthase | Nucleic acid substitution | Amino acid substitution | Primers |
|---|---|---|---|
| pPs619C1311 | GAA → GAT | E130D | SEQ ID NO: 15, 16 |
| | AGC → TTT | S477F | SEQ ID NO: 27, 28 |
| | CAG → ATG | Q481M | SEQ ID NO: 35, 36 |
| pPs619C1312 | GAA → GAT | E130D | SEQ ID NO: 15, 16 |
| | AGC → TTT | S477F | SEQ ID NO: 27, 28 |
| | CAG → CGC | Q481R | SEQ ID NO: 37, 38 |
| pPs619C1313 | GAA → GAT | E130D | SEQ ID NO: 15, 16 |
| | AGC → TAT | S477Y | SEQ ID NO: 29, 30 |
| | CAG → AAA | Q481K | SEQ ID NO: 33, 34 |
| pPs619C1314 | GAA → GAT | E130D | SEQ ID NO: 15, 16 |
| | AGC → TAT | S477Y | SEQ ID NO: 29, 30 |
| | CAG → ATG | Q481M | SEQ ID NO: 35, 36 |
| pPs619C1315 | GAA → GAT | E130D | SEQ ID NO: 15, 16 |
| | AGC → TAT | S477Y | SEQ ID NO: 29, 30 |
| | CAG → CGC | Q481R | SEQ ID NO: 37, 38 |

TABLE 5

| Recombinant synthase | Nucleic acid substitution | Amino acid substitution | Primers |
|---|---|---|---|
| pPs619C1400 | GAA → GAT | E130D | SEQ ID NO: 15, 16 |
| | AGC → ACC | S325T | SEQ ID NO: 17, 18 |
| | AGC → CGC | S477R | SEQ ID NO: 23, 24 |
| | CAG → ATG | Q481M | SEQ ID NO: 35, 36 |
| pPs619C1401 | GAA → GAT | E130D | SEQ ID NO: 15, 16 |
| | AGC → ACC | S325T | SEQ ID NO: 17, 18 |
| | AGC → CGC | S477R | SEQ ID NO: 23, 24 |
| | CAG → AAA | Q481K | SEQ ID NO: 33, 34 |
| pPs619C1334 | GAA → GAT | E130D | SEQ ID NO: 15, 16 |
| | AGC → ACC | S325T | SEQ ID NO: 17, 18 |
| | AGC → TTT | S477F | SEQ ID NO: 27, 28 |
| | CAG → ATG | Q481M | SEQ ID NO: 35, 36 |
| pPs619C1336 | GAA → GAT | E130D | SEQ ID NO: 15, 16 |
| | AGC → ACC | S325T | SEQ ID NO: 17, 18 |
| | AGC → GGC | S477G | SEQ ID NO: 31, 32 |
| | CAG → ATG | Q481M | SEQ ID NO: 35, 36 |
| pPs619C1339 | GAA → GAT | E130D | SEQ ID NO: 15, 16 |
| | AGC → ACC | S325T | SEQ ID NO: 17, 18 |
| | AGC → TTT | S477F | SEQ ID NO: 27, 28 |
| | CAG → AAA | Q481K | SEQ ID NO: 33, 34 |

Example 8

Preparation of P(3HB-co-LA) Using Various Mutants

Recombinant *E. Coli* being able to express PHA synthase mutant originated from *Pseudomonas* sp. 6-19 and propionyl-CoA transferase were constructed like the method described in the example 3, and used to prepare P(3HB-co-LA). Results were shown in tables 6, 7 and 8 below.

TABLE 6

| Mutation | WT | E130 | S325 | S477 | Q481 | Content (wt %) | LA mol % |
|---|---|---|---|---|---|---|---|
| Double | C1-202 | D | | | K | 36.6 | 35.3 |
| | C1-204 | D | | | M | 28.2 | 19.7 |
| | C1-204 | D | | | M | 42.9 | 10.7 |
| | C1-205 | D | | | R | 22.9 | 35.1 |

TABLE 7

| Mutation | WT | E130 | S325 | S477 | Q481 | Content (wt %) | LA mol % |
|---|---|---|---|---|---|---|---|
| Triple | C1-300 | D | T | | M | 43.8 | 31.9 |
| | C1-304 | D | | R | K | 20.2 | 22.0 |
| | C1-305 | D | | R | M | 51.8 | 15.2 |
| | C1-306 | D | | R | R | 23.5 | 26.8 |
| | C1-307 | D | | H | K | 36.9 | 31.0 |
| | C1-308 | D | | H | M | 47.0 | 27.6 |
| | C1-309 | D | | H | R | 28.5 | 39.8 |
| | C1-310 | D | | F | K | 60.4 | 15.0 |
| | C1-311 | D | | F | M | 49.2 | 32.3 |
| | C1-312 | D | | F | R | 57.9 | 13.2 |
| | C1-313 | D | | Y | K | 51.3 | 18.5 |
| | C1-314 | D | | Y | M | 50.8 | 29.3 |
| | C1-315 | D | | Y | R | 46.1 | 17.1 |

TABLE 8

| Mutation | WT | E130 | S325 | S477 | Q481 | Content (wt %) | LA mol % |
|---|---|---|---|---|---|---|---|
| Quadruple | C1-400 | D | T | R | M | 15.8 | 15.4 |
| | C1-401 | D | T | R | K | 12.9 | 12.5 |
| | C1-334 | D | T | F | M | 1.6 | 20.8 |
| | C1-336 | D | T | G | M | 10.3 | 17.5 |

As shown in tables 6, 7 and 8, the PHA synthase mutants of the present invention efficiently synthesized the lactate copolymer with lactyl-CoA as a substrate.

INDUSTRIAL APPLICABILITY

As described and proven above, the present invention provides a copolymer comprising 3-hydroxyalkanoate monomer unit and lactate monomer unit. The present invention also provides a method for preparing the copolymer, wherein the method comprises culturing a cell or plant comprising the gene of enzyme converting lactate and 3-hydroxyalkanoate into lactyl-CoA and 3-hydroxyalkanoyl-CoA, respectively, and polyhydroxyalkanoate (PHA) synthase gene together. The copolymer of the present invention is a biodegradable polymer being able to be usefully used instead of conventional synthetic plastic, and the copolymer can be used also for medical use.

What is claimed is:

1. A method for preparing a copolymer comprising a lactate monomer unit and a 3-hydroxyalkanoate monomer unit,
   wherein the method comprises culturing a microorganism comprising a gene encoding an enzyme converting lactate into lactyl-CoA, a gene encoding an enzyme converting 3-hydroxyalkanoate into 3-hydroxyalkanoyl-CoA, and a polyhydroxyalkanoate (PHA) synthase gene together, and
   wherein the PHA synthase gene encodes the amino acid sequence of SEQ ID NO: 8 having mutations of:
   a) S325T and Q481M;
   b) E130D and Q481K;
   c) S325T and Q481K;
   d) E130D and Q481M;
   e) E130D and Q481R;
   f) E130D, S325T and Q481M;
   g) E130D, S325T and Q481K;
   h) E130D, S477R and Q481K;
   i) E130D, S477R and Q481M;
   j) E130D, S477R and Q481R;
   k) E130D, S477H and Q481K;
   l) E130D, S477H and Q481M;
   m) E130D, S477H and Q481R;
   n) E130D, S477F and Q481K;
   o) E130D, S477F and Q481M;
   p) E130D, S477F and Q481R;
   q) E130D, S477Y and Q481K;
   r) E130D, S477Y and Q481M;
   s) E130D, S477Y and Q481R;
   t) E130D, S325T, S477R and Q481M;
   u) E130D, S325T, S477R and Q481K;
   v) E130D, S325T, S477F and Q481M;
   w) E130D, S325T, S477G and Q481M; or
   x) E130D, S325T, S477F and Q481K.

2. The method of claim 1,
   wherein the microorganism is obtained by transforming a microorganism not having a gene encoding an enzyme converting lactate into lactyl-CoA, and/or a gene encoding polyhydroxyalkanoate (PHA) synthase using lactyl-CoA as a substrate with a gene encoding an enzyme converting lactate into lactyl-CoA and/or a gene encoding polyhydroxyalkanoate (PHA) synthase using lactyl-CoA as a substrate.

3. The method of claim 1,
   wherein the gene encoding an enzyme converting lactate into lactyl-CoA is a propionyl-CoA transferase gene (pct).

4. The method of claim 1,
   wherein the polyhydroxyalkanoate (PHA) synthase gene is phaC1$_{ps6-19}$ derived from *Pseudomonas* sp. 6-19.

5. The method of claim 1,
wherein the microorganism further comprises a gene encoding alpha-ketothiolase (PhaA) and a gene encoding acetoacetyl-CoA reductase (PhaB).
6. The method of claim 1,
wherein the microorganism is *E. coli*.
7. The method of claim 1,
wherein the culturing is performed in a medium comprising 3-hydroxyalkanoate (3-HA).
8. The method of claim 7,
wherein the 3-hydroxyalkanoate is at least one selected from the group consisting of 3-hydroxybutyrate, 3-hydroxyvalerate, 3-hydroxypropionate and medium chain length (MCL) 3-hydroxyalkanoate.

* * * * *